United States Patent
Panchaud-Mirabel

(10) Patent No.: US 8,759,056 B2
(45) Date of Patent: Jun. 24, 2014

(54) METHOD FOR PRODUCING GRANULES CONTAINING FUNGI OF THE MONILIALES FAMILY

(75) Inventor: Elisabeth Panchaud-Mirabel, Toulouse (FR)

(73) Assignee: Urea Casale SA (CH)

( * ) Notice: Subject to any disclaimer, the term of this patent is extended or adjusted under 35 U.S.C. 154(b) by 1018 days.

(21) Appl. No.: 10/597,894

(22) PCT Filed: Feb. 8, 2005

(86) PCT No.: PCT/EP2005/001270
§ 371 (c)(1),
(2), (4) Date: Mar. 19, 2007

(87) PCT Pub. No.: WO2005/089556
PCT Pub. Date: Sep. 29, 2005

(65) Prior Publication Data
US 2007/0292932 A1  Dec. 20, 2007

(30) Foreign Application Priority Data
Mar. 15, 2004  (EP) .................................. 04006142

(51) Int. Cl.
*C12N 11/02* (2006.01)
*C12N 11/10* (2006.01)
*C12N 11/04* (2006.01)
*C12N 1/14* (2006.01)
*C12N 1/04* (2006.01)
*A01N 63/04* (2006.01)

(52) U.S. Cl.
USPC ........ 435/177; 435/178; 435/182; 435/254.1; 435/256.8; 435/260; 435/267; 424/93.5

(58) Field of Classification Search
CPC ........ C12N 11/02; C12N 11/04; C12N 11/10; C12N 1/14; C12N 1/04; A01N 63/04; C12R 1/645
See application file for complete search history.

(56) References Cited

U.S. PATENT DOCUMENTS

| | | | | |
|---|---|---|---|---|
| 3,791,927 | A | * | 2/1974 | Forgione et al. ............... 435/182 |
| 4,138,292 | A | * | 2/1979 | Chibata et al. ................. 435/178 |
| 4,668,512 | A | | 5/1987 | Lewis et al. |
| 4,818,530 | A | | 4/1989 | Marois et al. |
| 5,021,350 | A | * | 6/1991 | Jung et al. ...................... 435/243 |
| 5,053,332 | A | * | 10/1991 | Cook et al. ..................... 435/178 |
| 5,358,863 | A | | 10/1994 | Quimby, Jr. et al. |
| 5,730,973 | A | | 3/1998 | Morales et al. |
| 6,261,811 | B1 | * | 7/2001 | Hamdy ........................... 435/125 |

OTHER PUBLICATIONS

Jaffee et al., "Failure of a Mycelial Formulation of the Nematophagous Fungus *Hirsutella rhossillensis* to Suppress the Nematode *Heterodera schachtii*", Biological Control, vol. 6, Issue 3, 1996, pp. 340-346.

Lackey et al., "Alginate Pellet Formulation of *Hirsutella rhossillensis* for Biological Control of Plant-Parasitic Nematodes", Biological Control, vol. 3, 993, pp. 155-160.

|Jaffee et al., "Susceptibility of Root-Knot and Cyst Nematodes to the Nematode-Trapping Fungi *Monacrosporium ellipsosporum* and *M. cionopagum*", Soil Biology and Biochemistry, vol. 27, Issue 8, 1995. pp. 1083-1090.

Yang et al., "Evolution of Nematode-Trapping Cells of Predatory Fungi of the Orbiliaceae based on Evidence from rRNA-Encoding DNA and Multiprotein Sequences", PNAS, May 15, 2007, vol. 104, No. 20, pp. 8379-8384.

Boyettte et al., Production and Storage of Inoculum of Cerospora Kikuchil for Field Studies, Amer. Phylopathological Soc., 1985, vol. 75, No. 2, pp. 183-185.

Hebbar, Formulation of Mycoherbicidal Strains of *Fusarium oxysporum*, 1998, Weed Science, vol. 46, No. 4, pp. 501-507.

* cited by examiner

*Primary Examiner* — David M Naff
(74) *Attorney, Agent, or Firm* — Akerman LLP

(57) ABSTRACT

A process for the production of granules or pellets containing filamentous fungi is described comprising the steps of selecting and growing filamentous fungi in a suitable culture medium for a predetermined amount of time, adding a gelling agent and at least one carrier to said culture medium, so as to obtain a mixture, subjecting said mixture to gelling through contact, drop by drop, with a solution containing a calcium salt thus obtaining gelled pellets or granules containing said filamentous fungi and drying said gelled pellets or granules to a moisture content of 13-18%.

15 Claims, No Drawings

METHOD FOR PRODUCING GRANULES CONTAINING FUNGI OF THE MONILIALES FAMILY

FIELD OF APPLICATION

The present invention concerns the technical field of phytosanitary agents.

In particular, the invention concerns a process for the production on an industrial scale of granules or pellets containing filamentous fungi, more specifically nematophagus fungi.

PRIOR ART

The use of micro-organisms and in particular fungi as phytosanitary agents constitutes an increasingly common practice.

Fungi based products are already marketed for fighting insects, phytopathagenic fungi and other crop parasites.

For example, in U.S. Pat. No. 5,811,092 nematophagus agents are described for combating nematodes of the *Meloidogyne, Heterodera* and *Ditylenchus* genera, consisting of particular strains of *Arthrobotrys conoides Dreschsler*, a filamentous fungus.

The aforementioned nematodes are responsible for serious vegetable and fungal diseases and can cause huge economic losses, as they can lead to 50-70% of the harvest being compromised.

The use of nematophagus fungi, as an alternative to the usual anti-parasitic chemicals (for example methyl bromide, trichloronitromethane, dichloropropene, etc.), for application onto soil prior to cultivation, or to carbamates, applied to crops, allows serious inconveniences, such as sterilization of the soil, destruction of the ecological balance and potential toxicity to man and animals to be avoided.

Nematophagus fungi are therefore particularly suitable for use in organic farming, but there is currently a substantial difficulty in producing them industrially with high yields and in forms suitable to ensure a satisfactory state of preservation prior to use.

Indeed, in the prior art, nematophagus fungi are produced in a suitable culture medium. Then, the nematophagus fungi, together with their culture medium, are either directly dispersed on the soil to be treated or kept in the culture medium before use. However, in these conditions of preservation, the nematophagus fungi continue to reproduce rather quickly and decline after a short period of time (1-2 weeks) as the sources of nutrients are depleted.

The problem underlying the present invention was that of providing a process for industrial scale production of filamentous fungi, with high yields, low costs and in a form suitable for ensuring its stability and viability over long storage times prior to use on the soil to be treated.

SUMMARY OF THE INVENTION

The idea for solving such a technical problem was that of incorporating the filamentous fungi into suitable solid formulas that would ensure their stability and viability over long periods of time. In this regard, granular formulas or pellets containing filamentous fungi have proven suitable for the purposes of the present invention.

In the light of the aforementioned idea, the technical problem underlying the present invention is solved by a process for the production of granules or pellets containing filamentous fungi comprising the steps of:

selecting and growing filamentous fungi in a suitable culture medium for a predetermined amount of time, mixing said culture medium, after said predetermined amount of time, with a gelling agent and at least one carrier, so as to obtain a mixture, subjecting said mixture to gelling by drop by drop contact, with a solution containing a calcium salt, thus obtaining gelled pellets or granules containing said filamentous fungi, drying said gelled pellets or granules to a moisture content of 13-18%.

DETAILED DESCRIPTION OF THE INVENTION

The present invention shall be further described with reference to a number of example embodiments provided for illustrative and not limiting purposes.

Before proceeding with the illustration of the examples, it may be helpful to define the materials used to carry out the various steps of the production process according to the invention.

The filamentous fungi used in the process according to the invention belong to the Moniliales family, preferably filamentous fungi of *Arthrobotrys conoides* Dreschsler.

The culture medium for filamentous fungi comprises at least one carbon source chosen among the group consisting of molasses, malt extract and sucrose and at least one organic nitrogen source chosen between yeast extract and "corn steep liquor".

Preferably, the aforementioned at least one carbon source constitutes between 70 and 85% by weight of the dry weight of the culture medium and the aforementioned at least one organic nitrogen source constitutes between 15 and 30% by weight of the dry weight of the culture medium.

The culture medium can also include a mineral nitrogen source, consisting of ammonium nitrates or salts. The aforementioned mineral nitrogen source is usually added gradually to the culture medium during the growth of the fungi in an amount not greater than 10% by weight of the dry weight of the culture medium and usually between 5 and 8% by weight.

A preferred composition of the culture medium consists of 75-85% malt extract and 15-25% yeast extract, the percentages being by weight of the dry weight of the culture medium.

Another preferred culture medium comprises 60-65% molasses, 10-15% sucrose, 10-15% corn steep liquor and 10-15% yeast extract. Advantageously, such a culture medium contains, in addition, between 5 and 8% of a mineral nitrogen source, in particular diammonium hydrogen phosphate.

A further preferred culture medium contains two carbon sources, i.e. malt extract, in an amount of 25-30%, and molasses, in an amount of 40-45%, as well as corn steep liquor, in an amount of 25-30%.

The malt extract is obtained by germination of the cereal grains (usually barley). At the time of germination, specific enzymes (amylases) are produced, which allow the conversion of the starch into sugars. The malt extract contains about 60% maltose, vitamins and several micro-nutrients.

Molasses constitutes a by-product of the sugar industry and comes in the form of a brown-blackish viscous liquid, containing 10% water, 35% sucrose, 20% other sugars and 15% ash.

The yeast extract is obtained by *Saccharomyces cerevisiae* autolysis and comes in the form of fine pale yellow powder, easily soluble in water. The yeast extract contains peptides, free amino acids, purine and pyrimidine bases, as well as water-soluble vitamins of the B-group. The yeast extract has a total nitrogen content of 10% and an α-amminic nitrogen content of 5%.

The corn steep liquor is obtained through the steeping of corn grains at 50° C. for 24-48 hours in water containing sulphur dioxide. This reagent allows denaturation of the proteic network surrounding the starch grains and offers the advantage of preventing growth of undesirable micro-organisms during steeping. The corn steep liquor has a total nitrogen content of 7% and an α-amminic nitrogen content of 1.7% and also contains 5% sugars, 4% potassium, 3% phosphorus and 17% other minerals.

In the production process according to the invention, the growth of the filamentous fungus in the aforementioned culture media is preferably carried out over 5-10 days at a constant temperature of 23-30° C.

The gelling agent preferably consists of a solution containing sodium alginate at a concentration of 1-2%, preferably 1.3% by weight of the weight of the solution. Such a solution is preferably added to the culture medium of the filamentous fungus according to a culture medium:alginate solution volume ratio of between 40:60 and 60:40.

As known, sodium alginate can promote the gelling of a liquid mixture to which it is added, by contact of the mixture with a solution containing calcium salts.

An important aspect consists of the addition of carriers to the culture medium. In the present invention, by the term "carrier" we mean both a product providing stability and/or nutrients to the fungi dispersed in the granules so that they remain viable during storage until use, and a "filler", i.e. a product conferring the desired consistency and volume to the granules.

Preferably, the aforementioned carriers are selected from the group comprising diatom earth, flours and sugars.

A preferred carrier is Celaton FPM 0.08. It is a commercial product based upon diatom shells (siliceous single-celled algae) and has a granulometry of about 0.08 microns. This product can absorb a defined amount of water and therefore helps the achievement of a desired volume of the end granules.

Among the flours that can be used as carriers in the present invention, cornflour is the most preferred. It is a natural product capable of absorbing an amount of water equal to many times its volume and, in this specific case, also helps the achievement of a desired volume of the end granules. In addition, cornflour constitutes an important source of nutrients for the filamentous fungi dispersed in the granules during storage and when spreading the granules on the soil to be treated.

In particular, the use of cornflour as source of nutrients is particularly advantageous in the case of *Arthrobotrys conoides* Dreschsler, as, surprisingly, in such a case one can see that the fungus develops a greater number of nematodes traps with a consequent increase in efficacy in the fighting them.

Sugars advantageously allow the filamentous fungi to remain viable during storage, by stabilizing the cell membranes. Among the sugars that can be used in the process according to the invention, sucrose is especially preferred.

Preferably, in the present invention, the carriers are added to the culture medium via the gelling agent. In practice, by using a sodium alginate solution as a gelling agent, the carriers are preferably added to said sodium alginate solution in percentages ranging between 6% and 22% by weight of the weight of the solution. In a particularly preferred method the carriers are added to the sodium alginate solution in a percentage of 15% by weight of the weight of the solution.

In the process according to the invention, the gelling of the mixture containing the filamentous fungi and the relative culture medium as well as the gelling promoter and the carriers is preferably carried out by adding said mixture, drop by drop, to a calcium salt solution.

The calcium salt is preferably chosen between calcium chloride and calcium gluconate. The concentration of the calcium salt in the solution is between 0.2 M and 0.3 M and is preferably 0.25 M in the case of calcium chloride. Usually, the gelling proceeds faster with increasing calcium salt concentration.

The gelling granules or pellets that are formed by contact of the drops of the aforementioned mixture with the predetermined calcium salt solution are left to stand in the aforementioned solution for a predetermined amount of time, preferably 2-3 minutes, so as to complete the gelling. The removal of the gelled granules or pellets from the calcium salt solution is carried out in a conventional manner, for example by filtration.

The drying of the gelled granules or pellets can be advantageously carried out through sterile air flow at a temperature of 25-30° C. Generally, the gelled granules or pellets obtained from the gelling of the drops of mixture added to the predetermined calcium salt solution have a moisture content of 80-90%. Such a moisture content is reduced by means of drying to a value of 13-18%. In such a way, the granules reach the desired consistency and volume, also with the help of the carriers added previously to the culture medium.

Preferably, with the process according to the invention, granules or pellets having a diameter of 1-3 mm are obtained, which give an improved spread of the filamentous fungi over the soil to be treated.

The process according to the invention can advantageously be carried out on an industrial scale through apparatus that are inexpensive and easy to design. A suitable apparatus, briefly described hereafter as a non-limiting example, comprises a reactor for the growth of the desired filamentous fungi in the suitable culture medium, a mixer in which the gelling agent and the carriers are mixed with the culture medium so as to form a mixture, means suitable for feeding measured amounts of the mixture to suitable perforated elements so as to form drops of the mixture having a predetermined volume, a vessel containing an aqueous calcium salt solution to collect the aforementioned drops and allow their gelling, and a drier to dry the gelled granules or pellets recovered in the vessel containing the aqueous calcium salt solution.

The means for feeding measured amounts of the mixture can, for example, comprise a peristaltic pump or similar devices whereas the perforated elements can be tubes each terminating at the bottom with a hole of predetermined diameter, for example 1-4 mm.

It is important that the aforementioned apparatus operates in sterile conditions in order to avoid contamination by microorganisms, in particular those antagonistic to the desired filamentous fungi. The products used to carry out the process according to the invention, in particular the products added to the culture medium in the mixture should also be suitably sterilized before use.

The granules or pellets obtained according to the process of the invention are ready for use but advantageously the filamentous fungi contained in them remain stable and viable for long periods of time. The aforementioned granules or pellets thus lend themselves to being preserved or stored for a long time prior to use after which the filamentous fungi maintain a totally satisfactory viability for the applications for which they are intended.

The duration of the preservation time of the granules or pellets according to the invention before use is advantageously greater than 8 weeks and is generally between 4 and 6 months.

The following examples of actuation of the process according to the invention were carried out with filamentous fungi of the Moniliales family, and preferably *Arthrobotrys conoides* Dreschsler filamentous fungi.

EXAMPLE 1

Culturing of the filamentous fungus was carried out in a 2 liter reactor containing 1.2 liters of culture medium.

The reactor preferably consists of a container having a rounded bottom, provided with a blade agitator, heating and cooling means, air blowing means, as well as pH, $O_2$ and temperature probes.

The medium consisted of 20 g/l of malt extract and 4 g/l of yeast extract and was sterilized before being seeded with conidia of the fungus in question.

The culture was incubated for 6 days from seeding at a temperature of about 27° C.

During incubation, samples were taken from the culture medium to determine the dry mass (g/l) and the number of propagules (CFU/l). To determine the dry mass, 20 ml of the culture medium were filtered and then dried in an oven at 100° C. for 24 hours. The number of propagules was determined on 1 ml of culture media.

At the end of the incubation time almost 8 g/l of fungi are thus obtained with a number of propagules of $6 \times 10^9$ per liter.

The culture medium containing the fungi is then transferred into a mixer and 1800 ml of an aqueous solution at 1.3% by weight of sodium alginate, to which solution 6.6% of Celaton FPM 0.08 (by weight of the weight of the solution) has been added, is added to the culture medium.

The resulting mixture is then homogenized in the mixer and added, drop by drop, through a perforated tube (diameter of the hole 1.6 mm) into a vessel containing a 0.25 M calcium chloride solution.

Gelled granules of the aforementioned mixture are thus obtained that are left to stand in the calcium chloride solution for 3 minutes.

At the end of the standing time, the gelled granules are separated by decanting and are dried on a conveyor belt to a moisture content of 17%. The average diameter of the dry granules is 2.2 mm.

The average number of propagules in the dry granules, as determined immediately after their formation, is substantially the same as that determined at the end of incubation of the filamentous fungus proving that the aforementioned propagules have entirely survived the granulation process of the present invention.

The aforementioned dry granules are kept for 3 months at room temperature. At the end of the storage period, the average number of surviving propagules is equal to 50% of that determined after granule formation.

EXAMPLE 2

The test of example 2 was repeated using the same experimental conditions as example 1 with the exception that 1800 ml of an aqueous solution at 1.3% by weight of sodium alginate, to which solution 6.6% of Celaton FPM 0.08 and 3.3% of cornflour (by weight of the weight of the solution) had been added, was added to the culture medium.

The average diameter of the dry granules is 2.5 mm and their moisture content was 17%.

The average number of propagules in the dry granules, as determined immediately after their formation, is substantially the same as that determined at the end of incubation of the filamentous fungus proving that the aforementioned propagules have entirely survived the granulation process of the present invention.

The aforementioned dry granules are kept for 3 months at room temperature. At the end of the storage period, the average number of surviving propagules is equal to 90% of that determined after granule formation, which allows the dry granules to be able to be effectively used on soil as phytosanitary agents.

EXAMPLE 3

The test of example 3 was repeated using the same experimental conditions as example 1 with the exception that 1800 ml of an aqueous solution at 1.3% by weight of sodium alginate, to which solution 6.6% of Celaton FPM 0.08, 3.3% of cornflour and 5% of sucrose (by weight of the weight of the solution) had been added, was added to the culture medium.

The average diameter of the dry granules is 2.9 mm and their moisture content is 17%.

The average number of propagules in the dry granules, as determined immediately after their formation, is substantially the same as that determined at the end of incubation of the filamentous fungus proving that the aforementioned propagules have entirely survived the granulation process of the present invention.

The aforementioned dry granules are kept for 3 months at room temperature. At the end of the storage period, the average number of surviving propagules is equal to 100% of that determined after granule formation, which allows the dry granules to be able to be effectively used on soil as phytosanitary agents.

Moreover, in the use of the aforementioned granules, there is a greater efficacy of the fungus in combating nematodes due to the fact that the fungus develops a greater number of traps against them.

The invention claimed is:

1. A process for the production of granules containing filamentous fungi of the Moniliales family comprising the steps of:
    selecting and growing filamentous fungi of the Moniliales family in a suitable culture medium for a predetermined amount of time,
    mixing said culture medium, after said predetermined time, with a gelling agent and at least one carrier material, so as to obtain a mixture,
    subjecting said mixture to gelling through drop by drop contact, with a solution containing a calcium salt thus obtaining gelled granules containing said filamentous fungi, and
    drying said gelled granules to a moisture content of 13-18%,
    wherein said culture medium for filamentous fungi comprises at least one carbon source selected from the group consisting of molasses, malt extract and sucrose, and at least one organic nitrogen source selected from the group consisting of yeast extract and corn steep liquor.

2. The process according to claim 1, wherein said gelling step is carried out by adding said mixture, drop by drop, into said solution containing a calcium salt.

3. The process according to claim 1, wherein said at least one carbon source constitutes between 70 and 85% by weight of the dry weight of the culture medium and said at least one organic nitrogen source constitutes between 15 and 30% by weight of the dry weight of the culture medium.

4. The process according to claim 1, wherein said culture medium further comprises a mineral nitrogen source.

5. The process according to claim 4, wherein said mineral nitrogen source is contained in an amount not greater than 10% by weight of the dry weight of the culture medium.

6. The process according to claim 1, wherein the gelling agent consists of a solution containing between 1 and 2% by weight of sodium alginate.

7. The process according to claim 6, wherein said sodium alginate solution is added to the culture medium of the filamentous fungus according to a culture medium/alginate solution volume ratio of between 40:60 and 60:40.

8. The process according to claim 1, wherein said carrier material is selected from the group consisting of diatom earth, flours, and sugars, and combinations thereof.

9. The process according to claim 8, wherein said filamentous fungi are of *Arthrobotrys conoides* Dreschsler and said carrier material comprises at least cornflour.

10. The process according to claim 8, wherein the carrier material is added to the sodium alginate solution in percentages ranging between 6% and 22% by weight of the weight of the solution.

11. The process according to claim 1, wherein the solution containing a calcium salt is an aqueous calcium chloride or calcium gluconate solution having a concentration of 0.2-0.3 M.

12. The process according to claim 1, wherein the dried granules have an average diameter of between 1 and 3 mm.

13. The process according to claim 5, wherein said mineral nitrogen source is contained in an amount between 5 and 8% by weight of the dry weight of the culture medium.

14. The process according to claim 8, wherein said flours include cornflour.

15. The process according to claim 8, wherein said carrier material comprises cornflour and sucrose.

* * * * *